United States Patent [19]

Harley

[11] Patent Number: 4,816,609

[45] Date of Patent: Mar. 28, 1989

[54] PROCESS AND CATALYST FOR THE DEHYDROHALOGENATION OF HALOGENATED HYDROCARBONS

[75] Inventor: A. Dale Harley, Midland, Mich.

[73] Assignee: The Dow Chemical Company, Midland, Mich.

[21] Appl. No.: 53,925

[22] Filed: May 26, 1987

[51] Int. Cl.$^4$ .................... C07C 17/34; C07C 21/06
[52] U.S. Cl. ................................ 570/226; 570/204; 570/227; 570/228
[58] Field of Search ............... 570/204, 220, 226, 227, 570/228, 229, 205

[56] References Cited

FOREIGN PATENT DOCUMENTS

| 146520 | 9/1983 | Japan | 570/226 |
|---|---|---|---|
| 1197531 | 9/1986 | Japan | 570/226 |
| 1197532 | 9/1986 | Japan | 570/226 |
| 722892 | 3/1980 | U.S.S.R. | 570/226 |
| 791792 | 3/1958 | United Kingdom | 570/226 |

*Primary Examiner*—Werren B. Lone

[57] ABSTRACT

An unsaturated halohydrocarbon such as vinylidene chloride is produced by the dehydrohalogenation of haloalkanes such as 1,1,1-trichloroethane or 1,1,2-trichloroethane, in the presence of a novel mixed salt catalyst containing a Group IA metal cation such as Cs, a Group IIA metal cation such as Mg and a neutralizing number of counter anions such as chloride distributed on a support such as silica.

9 Claims, No Drawings

PROCESS AND CATALYST FOR THE DEHYDROHALOGENATION OF HALOGENATED HYDROCARBONS

BACKGROUND OF THE INVENTION

This invention relate to the dehydrohalogenation of halogenated hydrocarbons. More specifically, it pertains to a process and a catalyst for the dehydrohalogenation of halogenated hydrocarbons to produce the corresponding unsaturated halohydrocarbon or unsaturated hydrocarbon.

Unsaturated halohydrocarbons and unsaturated hydrocarbons are extremely useful for the preparation of various polymeric compositions. For example, 1,1-dichloroethene, commonly known as vinylidene chloride, can be used to produce vinylidene chloride polymers. Vinylidene chloride polymers have an extremely high barrier resistance to the transmission of oxygen and water vapors. Thus, such polymers, particularly copolymers of vinylidene chloride and vinyl chloride, acrylates or other monomers, are very useful as films or coatings in food packaging composites. Other copolymers produced from vinylidene chloride show excellent resistance to solvents and corrosive chemicals and have a high degree of abrasion resistance, toughness and dimensional stability. Such durable copolymers are extremely useful in rigid extrusions, tank linings, monofilaments, and paint and cement additives.

U.S. Pat. No. 3,984,489 describes a process for preparing vinylidene chloride by the caustic dehydrochlorination of 1,1,2-trichloroethane in the presence of an amine. This caustic cracking of a chlorinated hydrocarbon leads to the formation of a salt stream which leads to waste deposit problems and causes the loss of chlorine.

U.S. Pat. Nos. 2,765,340; 2,803,678 and 2,803,679 describe a dehydrochlorination process utilizing a metal salt or metal oxide as a catalyst. U.S. Pat. No. 3,230,181 describes a dehydrohalogenation process utilizing calcium bromide as a catalyst. United Kingdom patent application No. 2,008,117A describes the preparation of vinylidene chloride by the vapor phase dehydrochorination of 1,1,2-trichloroethane in the presence of a cesium halide catalyst. U.S. Pat. Nos. 4,144,192 and 4,225,519 describe the dehydrochlorination of 1,1,2-trichloroethane in the presence of a cesium nitrate catalyst. U.S. Pat. No. 3,870,762 discloses a vapor phase dehydrochlorination process utilizing a chloride or fluoride of potassium, rubidium or cesium.

The above processes utilizing a catalyst suffer from deactivation of the catalyst due to the formation of coke on the catalyst surface. The formation of by-products and/or low selectivity to the desired products are also continuing problems in dehydrohalogenation reactions in general.

What is needed is an efficient dehydrohalogenation process that would avoid the waste disposal and halogen loss problems of prior methods by providing a means for safely and economically removing any salt or hydrogen halide produced by the dehydrohalogenation reaction. A process is also needed that would utilize a catalyst which would not rapidly deactivate due to coke deposition on the catalyst surface. A process is also needed that would provide for a high selectivity of the desired dehydrohalogenated product.

SUMMARY OF THE INVENTION

The present invention is a catalyst and process for using such catalyst that solves many of the aforementioned problems inherent in conventional dehydrohalogenation methods. The catalyst of the present invention is a compound comprising a Group IA metal cation, a Group IIA metal cation and a neutralizing number of counter anions supported on a porous carrier material. It has surprisingly been found that such a catalyst does not rapidly deactivate in typical dehydrohalogenation reactions when the catalyst is used in the presence of an alkanol and oxygen. The catalyst of the present invention also provides for high selectivity of the desired dehydrohalogenated product.

The process of present invention comprises contacting a halogenated hydrocarbon and an alkanol in the presence of the catalyst described hereinbefore under reaction conditions sufficient to form the corresponding unsaturated halohydrocarbon or unsaturated hydrocarbon. It has been discovered that this process is highly selective and provides for the capture of the halogen as it is removed from the halogenated hydrocarbon, thereby avoiding expensive waste of the halogen. The process of the present invention, when practiced in the presence of an oxygen source, also avoids deactivation of the catalyst due to coke formation on the catalyst surface.

DETAILED DESCRIPTION OF ILLUSTRATIVE EMBODIMENTS

The catalyst of the present invention is advantageously a salt of a Group IA metal (alkali metal), a Group IIA metal (alkaline earth metal) and a neuralizing number of counter anions supported on a porous carrier material. Preferable Group IA metals include potassium, rubidium and cesium, with cesium being most preferred. The Group IIA metals are preferably magnesium, calcium, strontium and barium, with magnesium being most preferred. While any counter anion is suitable in the catalyst of this invention, such as bromide, chloride and fluoride, the halides are preferred, with chloride being most preferred. Other suitable anions are nitrates, sulfate, phosphate, acetates, oxalate and cyanides.

The amount of Group IA metal in the salt is suitably that amount which is equimolar to that of Group IIA. The Group IA metal preferably constitutes from about 15 to about 45 weight percent of the total salt, more preferably from about 20 to about 30 weight percent of the total salt. The amount of Group IIA metal in the salt is suitably that amount which is equimolar to that of Group IA. The Group IIA metal is preferably present in an amount ranging from about 4 to abou 25 weight percent of the total salt, more preferably from about 4 to about 10 weight percent of the total salt. The amount of counter anion is that which is sufficient to neutralize the cations of the salt. The counter anion is preferably present in an amount ranging from about 10 to about 35 weight percent of the total salt, preferably from about 15 to about 25 weight percent.

Any support which will withstand the dehydrohalogenation conditions described herein can be used in the process of the present invention. Examples of appropriate supports include the well-known carbon supports such as activated carbon, carbon black, chars and coke. Other suitable supports that may be used to support the catalyst include pumice, silica gel, asbestos, diatomaceous earth, fullers earth, alumina, titania, zirconia, silica-alumina, magnesia, magnesium silicate, silicon carbide, silicalite and silica. Preferred supports include alumina and silica, with silica being the most preferred. A silica having a surface area between 100 m²/g and 300 m²/g and a pore volume in the range of 0.75 cc/g to 1.4 cc/g is particularly active in the process of the present invention.

The salt is suitably supported on the carrier material by any standard impregnation technique such as that disclosed in *Experimental Methods in Catalytic Research*, Vol. II, edited by R. B. Anderson and P. T. Dawson, Academic Press, New York, 1978. A solution of both the Group IA and Group IIA metal ions and the associated anions may be employed to impregnate the support material or the metal salts may be impregnated from separate solutions. The resulting catalyst comprising the catalytically active salt and the support preferably comprises from about 1 to about 50 weight percent of the salt, with from about 20 to about 30 weight percent of the salt being most preferred.

The process of the present invention comprises contacting a halogenated hydrocarbon and an alkanol in the presence of the aforementioned catalyst under reaction conditions sufficient to form the corresponding unsaturated halohydrocarbon or unsaturated hydrocarbon. The halogenated hydrocarbons of the present invention may be aliphatic, cyclic, saturated, unsaturated or aromatic. The halogenated hydrocarbons of the present invention all contain in an aliphatic or alicyclic portion of the molecule the radical:

wherein X is chloro, bromo, iodo or fluoro, preferably chloro. Examples of such halohydrocarbons include 1,1,1-trichloroethane, 1,1,2-trichloroethane, 1,1-dichloroethane, 1,2-dichloroethane, 1,2-dichloropropane, 1,2,3-trichloropropane, 1,1,1-tribromoethane, α-chlorostyrene, 1,1,1-trifluoroethane and 1,1,1-difluorochloroethane. Of these halohydrocarbons, 1,1,2-trichloroethane, 1,2-dichloropropane and 1,2,3-trichoropropane are preferred, with 1,1,2-trichloroethane being most preferred.

Any alkanol can be utilized that will allow the dehydrohalogenation described herein to proceed. Typical alkanols useful for the present invention include methanol, ethanol, propanol, isopropanol, butanol, sec-butanol, tert-butanol and pentanol with methanol and ethanol being preferred. The most preferred alkanol in the process of the present invention is methanol.

The ratio of alkanol to halogenated hydrocarbon is in the range from about 0.1:100 to about 100:0.1. The preferred ratio is in the range from about 1:1 to about 4:1, with the most preferred ratio being 2:1.

The process may be carried out at any temperature at which dehydrohalogenation will occur. Suitable temperatures are in the range from about 25° C. to about 475° C., with between about 275° C. and about 375° C. being preferred. The reaction can be carried out at any pressure which does not interfere with the productivity of the catalyst. Typical pressures employed in the present invention are in the range from about 14 psi to about 500 psi. Preferably, the pressure is in the range from about 35 psi to about 100 psi.

In preferred practice of the invention, the halohydrocarbon is dehydrochlorinated by contacting a vaporous feed of the halohydrocarbon with the catalyst at elevated temperature and atmospheric pressure to superatmospheric pressure for a time sufficient to effect the desired degree of conversion of the haloghydrocarbon. The vaporous feed is preferably a mixture of the halohydrocarbon and the alcohol. While the invention is not to be bound by any mechanical theory, the alcohol in this process is believed to serve as a hydroxide donor and a halide acceptor and thereby functions to regenerate the catalyst and to recover the halide value as an alkyl halide. In the vapor phase, the presence of from about 2 to about 5 weight percent oxygen in nitrogen serves to extend the life of the catalyst to more than 200 hours. The oxygen preferably comprises from about 0.01 to about 1.0 weight percent of the entire vaporous feed. The contact time of the vaporous mixture with the catalyst in the reactor is generally not more than about 3 minutes, preferably not more than about 30 seconds. Suitable superficial gas hourly space velocities (GHSV) for the vaporous feed are those which effect the desired conversion and selectivities. Preferably such GHSV is in the range from about 100 to about 10,000 hours$^{-1}$, most preferably from about 300 to about 3,000 hours$^{-1}$. The catalyst can be employed in the form of a packed bed or a fluidized bed.

In an especially preferred embodiment of the invention, 1,1,2-trichloroethane is converted to vinylidene chloride in yields greater than 80 percent, most preferably greater than 55 percent, with less than 20 percent, most preferably less than 10 percent of cis and trans-1,2-dichloroethane being formed.

SPECIFIC EMBODIMENTS

The following examples are included for illustrative purposes only and are not intended to limit the limit the scope of the claims. All parts and percentages are by weight unless otherwise indicated.

Catalyst Preparation:

To 13.97 g (0.083 mole) of CsCl is added 16.85 g (0.083 mole) of MgCl$_2$ 6H$_2$O. The mixture is dissolved in 52 ml of water. The solution is then added to 20.0 g of SiO$_2$ (particle size 0.59–1.17 mm, surface area 185 m²/g, pore volume 1.4 cc/g) and air dried at 120° C. for 24 hours. The catalyst comprises 26.28 percent of Cs, 21.15 percent of Cl, 4.76 percent of Mg and a remaining percentage of silica.

EXAMPLE 1

A Hastalloy B tubular reactor (30.5 cm × 1.27 cm) containing 9.45 g (15.0 cc) of CsMgCl$_3$6H$_2$O supported on silica gel is pretreated for 2 hours with a mixture of 2.07 percent O$_2$ in N$_2$ and H$_2$O at 425° C. with a flow rate of 50 cc/min for 2 hours. The temperature of the reactor is decreased to 325° C. To the reactor is then fed a premixed solution of 101.43 ml of methanol and 211.17 ml of 1,1,2-trichloroethane at a rate of 10 ml/min. for 200 hours. The downstream product lines are heated to 180° C. to maintain the system in the vapor phase and the product is sampled periodically by a gas chromatograph. The effluent gases are condensed at −78° C. with a dry ice trap and the remaining volatiles are scrubbed with a 6N NaOH solution and vented.

EXAMPLES 2-8

Several catalysts are prepared in accordance with the method of Example 1. The catalysts are subjected to the same methanol/trichloroethane treatment as described in Example 1. The catalysts and their respective results are shown in Table I.

TABLE I

| Sample No. | Catalyst[1] | Selectivity[2] VC[4] | Cis-1,2 DCE[4] | Trans-1,2 DCE[4] | % conversion[3] |
|---|---|---|---|---|---|
| 1 | $CsMgCl_3$ | 80.1 | 11.5 | 10.2 | 88.6 |
| 2 | $CsBaCl_3$ | 85.0 | 6.9 | 8.0 | 50.3 |
| 3 | $Cs(Ca,Mg)Cl_3$ | 79.4 | 9.7 | 10.9 | 84.3 |
| 4 | $Cs(Ba,Mg)Cl_3$ | 81.7 | 8.1 | 10.1 | 89.5 |
| 5 | $Cs_2MgCl_4$ | 65.6 | 14.2 | 14.1 | 81.2 |
| 6 | $CsMgFCl_2$ | 67.1 | 18.1 | 15.4 | 99.4 |
| $C_1$* | $MgCl_2$ | 8.3 | 13.2 | 78.4 | 34.4 |
| $C_2$* | $CsCl$ | 67.0 | 10.6 | 22.3 | 7.5 |

[1] All salts supported on silica gel at a total salt concentration in the catalyst of about 50 percent.
[2] Selectivity is based on weight of vinylidene chloride produced divided by the weight of trichloroethane consumed.
[3] % Conversion = % of 1,1,2-trichloroethane converted to products
[4] VC is Vinylidene chloride and DCE is Dichloroethylene
*Not an example of the invention.

As evidenced by the data in Table I, the use of a mixed salt catalyst as in Sample Nos. 1-6 produces the desired vinylidene chloride in greater quantities than do the single salt catalysts of Sample Nos. $C_1$ and $C_2$.

What is claimed is:

1. A process for dehydrohalogenating 1,1,2-trichloroethane which process comprises contacting the 1,1,2-trichloroethane and an alkanol in the presence of a catalytic amount of a catalyst in the form of a complex comprising a Group IA metal cation, a Group IIA metal cation and a neutralizing number of at least one counter anion selected from the group consisting of halide, nitrate, sulfate, phosphate, acetate, oxalate, and cyanide, on a porous support under reaction conditions sufficient to form vinylidene chloride.

2. The process of claim 1 wherein the Group IA metal of the catalyst is cesium.

3. The process of claim 1 wherein the Group IIA metal of the catalyst is magnesium.

4. The process of claim 1 wherein the counter anion(s) of the catalyst complex is (are) chloride.

5. The process of claim 1 wherein the porous carrier material of the catalyst is silica.

6. The process of claim 5 wherein the silica has a surface area between 100 $m^2/g$ and 300 $m^2/g$ and a pore volume between 0.75 cc/g and 1.4 cc/g.

7. The process of claim 1 wherein the alkanol is methanol.

8. The process of claim 1 wherein the counter anion is halide.

9. A process for preparing vinylidene chloride comprising (a) preparing $CsMgCl_3 6H_2O$ by dissolving CsCl and $MgCl_2 6H_2O$ in $H_2O$; (b) impregnating the $CsMgCl_3 6H_2O$ onto a silica gel having a particle size between 0.59 and 1.17 mm, a surface area of 185 $m^2/g$ and a pore volume of 1.4 cc/g; (c) pretreating a corrosion-resistant reactor with a mixture of 2.07 percent $O_2$ in $N_2$ and $H_2$ at 425° C. with a flow rate of 50 cc/min for 2 hours; (d) decreasing the reactor temperature to 325° C.; and (e) feeding to the reactor a premixed stream of methanol and 1,1,2-trichloroethane at a rate of 2-5 ml/min for 200 hours.

* * * * *